(12) United States Patent
Kawabata et al.

(10) Patent No.: US 11,712,166 B2
(45) Date of Patent: Aug. 1, 2023

(54) SPHYGMOMANOMETER, AND METHOD AND DEVICE FOR BLOOD PRESSURE MEASUREMENT

(71) Applicants: OMRON CORPORATION, Kyoto (JP); OMRON HEALTHCARE CO., LTD., Muko (JP)

(72) Inventors: Yasuhiro Kawabata, Kyoto (JP); Kentaro Mori, Kyoto (JP); Naomi Matsumura, Kyoto (JP)

(73) Assignees: OMRON CORPORATION, Kyoto (JP); OMRON HEALTHCARE CO., LTD., Muko (JP)

( * ) Notice: Subject to any disclaimer, the term of this patent is extended or adjusted under 35 U.S.C. 154(b) by 101 days.

(21) Appl. No.: 16/441,066

(22) Filed: Jun. 14, 2019

(65) Prior Publication Data

US 2019/0290141 A1    Sep. 26, 2019

Related U.S. Application Data

(63) Continuation of application No. PCT/JP2017/040053, filed on Nov. 7, 2017.

(30) Foreign Application Priority Data

Dec. 28, 2016 (JP) ................................. 2016-255262

(51) Int. Cl.
*A61B 5/022* (2006.01)
*A61B 5/021* (2006.01)
(Continued)

(52) U.S. Cl.
CPC ............ *A61B 5/02225* (2013.01); *A61B 5/02* (2013.01); *A61B 5/022* (2013.01); *A61B 5/0225* (2013.01);
(Continued)

(58) Field of Classification Search
CPC ....................... A61B 5/02108; A61B 5/02125
(Continued)

(56) References Cited

U.S. PATENT DOCUMENTS

| | | | | |
|---|---|---|---|---|
| 2002/0002340 A1* | 1/2002 | Nishibayashi | ..... | A61B 5/02225 |
| | | | | 600/494 |
| 2003/0167014 A1* | 9/2003 | Ogura | .................... | A61B 5/021 |
| | | | | 600/513 |

(Continued)

FOREIGN PATENT DOCUMENTS

| | | |
|---|---|---|
| CN | 103222860 A | 7/2013 |
| CN | 105796070 A | 7/2016 |

(Continued)

OTHER PUBLICATIONS

Feb. 13, 2018 International Search Report issued in International Patent Application No. PCT/JP2017/040053.

(Continued)

*Primary Examiner* — Jacqueline Cheng
*Assistant Examiner* — Tho Q Tran
(74) *Attorney, Agent, or Firm* — Oliff PLC

(57) ABSTRACT

A sphygmomanometer includes: a first fluid bag that is to be worn around a measurement site; first and second pulse wave sensors that are mounted on first fluid bag, and detect pulse waves of respective opposing areas of an artery running along measurement site; pressing parts that locally presses areas corresponding to first and second pulse wave sensors from an outer circumference side, opposite of an inner circumference side of first fluid bag where first and second pulse wave sensors are mounted. Blood pressure is calculated based on pulse transit time obtained from outputs from first and second pulse wave sensors, with first fluid bag in an unpressurized state and first and second pulse wave sensors being pressed by a pressing force of the pressing (Continued)

part. Blood pressure is calculated, for oscillometric blood pressure measurement, based on pressure within first fluid bag with first fluid bag in a pressurized state.

5 Claims, 11 Drawing Sheets

(51) Int. Cl.
    *A61B 5/00*       (2006.01)
    *A61B 5/02*       (2006.01)
    *A61B 5/0225*     (2006.01)
    *A61B 5/0235*     (2006.01)

(52) U.S. Cl.
    CPC ...... *A61B 5/02108* (2013.01); *A61B 5/02141* (2013.01); *A61B 5/681* (2013.01); *A61B 5/0235* (2013.01); *A61B 5/02233* (2013.01); *A61B 2562/0219* (2013.01); *A61B 2562/0247* (2013.01)

(58) Field of Classification Search
    USPC ........................................................ 600/492
    See application file for complete search history.

(56) References Cited

U.S. PATENT DOCUMENTS

| | | | | |
|---|---|---|---|---|
| 2005/0015015 | A1* | 1/2005 | Mizukoshi | A61B 5/02233 600/499 |
| 2005/0283084 | A1* | 12/2005 | Kato | 600/499 |
| 2010/0076328 | A1* | 3/2010 | Matsumura | A61B 5/6843 600/500 |
| 2012/0253209 | A1* | 10/2012 | Ukawa | A61B 5/02133 600/494 |
| 2013/0165787 | A1* | 6/2013 | Ukawa | A61B 8/0825 600/443 |
| 2017/0188973 | A1* | 7/2017 | Banet | A61B 5/316 |
| 2017/0251934 | A1* | 9/2017 | Ohno | A61B 5/0245 |
| 2017/0273579 | A1* | 9/2017 | Mori et al. | A61B 5/02108 |
| 2019/0046051 | A1* | 2/2019 | Kato et al. | A61B 5/0225 |
| 2019/0209031 | A1* | 7/2019 | Ariyama | A61B 5/352 |
| 2019/0365257 | A1* | 12/2019 | Lee | A61B 5/02141 |

FOREIGN PATENT DOCUMENTS

| | | | | |
|---|---|---|---|---|
| JP | H10-328151 | A | 12/1998 | |
| JP | 2007-44364 | A | 2/2007 | |
| JP | 2008-136655 | A | 6/2008 | |
| JP | 2012-130362 | A | 7/2012 | |
| WO | WO-2011105195 | A1 * | 9/2011 | ......... A61B 5/02007 |
| WO | WO-2016040253 | A1 * | 3/2016 | ............. A61B 5/021 |

OTHER PUBLICATIONS

May 8, 2021 Office Action issued in Chinese Patent Application No. 201780075967.8.

* cited by examiner $$r = \frac{\sum_{i=1}^{n}(x_i - \bar{x})(y_i - \bar{y})}{\{(\sum_{i=1}^{n}(x_i - \bar{x})^2)(\sum_{i=1}^{n}(y_i - \bar{y})^2)\}^{1/2}} \quad \cdots (Eq.1)$$

$$EBP = \frac{\alpha}{DT^2} + \beta \quad \cdots (Eq.2)$$

$$EBP = \frac{\alpha}{DT^2} + \frac{\beta}{DT} + \gamma DT + \delta \quad \cdots (Eq.3)$$

$$EBP = \frac{\alpha}{DT} + \beta RR + \gamma VR + \delta \quad \cdots (Eq.4)$$

SPHYGMOMANOMETER, AND METHOD AND DEVICE FOR BLOOD PRESSURE MEASUREMENT

CROSS-REFERENCE TO RELATED APPLICATION

This is a continuation application of International Application No. PCT/JP2017/040053, with an International filing date of Nov. 7, 2017, which claims priority of Japanese Patent Application No. 2016-255262 filed on Dec. 28, 2016, the entire content of which is hereby incorporated by reference.

TECHNICAL FIELD

The present invention relates to a sphygmomanometer and a method for blood pressure measurement, and more specifically to a sphygmomanometer capable of measuring blood pressure based on pulse transit time (PTT), which is the time it takes a pulse wave to propagate through an artery, and oscillometric blood pressure, and a method for blood pressure measurement. Also, the present invention relates to a device having a blood pressure measurement function.

BACKGROUND ART

For example, as described in Patent Literature 1 (Japanese Patent Application Publication No. Hei 10-328151), a technology of arranging first and second pressure sensors along a radial artery, and pressing the first and second pressure sensors with an air bag via a pressing plate toward the wrist is known. This technology measures a pulse transit time, which is a time difference between pulse wave signals detected by the first pressure sensor and the second pressure sensor, and measures blood pressure based on the pulse transit time.

SUMMARY OF THE INVENTION

When blood pressure is measured based on pulse transit time as in Patent Literature 1, parameters necessary for calculating blood pressure at rest need to be optimized for each subject. Even with such optimization, the relationship between a pulse transit time and blood pressure varies depending on the measurement conditions, and this necessitates calibration with blood pressure that is measured using an oscillometric sphygmomanometer.

Thus, aside from a device that measures blood pressure based on a pulse transit time, an oscillometric sphygmomanometer for calibration has so far been prepared for blood pressure measurement. This has been very inconvenient for subjects. Thus, measuring these different types of blood pressures with a single device has long been awaited.

For example, an oscillometric sphygmomanometer cuff that is worn around a wrist of a subject may be provided around and over the first and second pressure sensors, the pressing plate, and the air bag of Patent Literature 1, and oscillometric blood pressure may be measured using this cuff.

However, in this case, the first and second pressure sensors and the pressing plate are present between the cuff and the wrist, and thus these hard members hinder the cuff from pressing the wrist to sufficiently close the blood vessel. This produces a problem of reduction in accuracy of blood pressure measurement.

The present invention thus objects to provide a sphygmomanometer having a simple structure and capable of accurately measuring both pulse transit time-based blood pressure and oscillometric blood pressure, and a method and a device for blood pressure measurement.

To achieve the objects, a sphygmomanometer of the present disclosure is a sphygmomanometer including:

a first fluid bag that is to be worn around a measurement site, and turns into a pressurized state or an unpressurized state by supply or discharge of fluid, first and second pulse wave sensors that are mounted on the first fluid bag in a manner to be spaced from each other with respect to the width direction of the first fluid bag, and detect pulse waves of the respective opposing portions of an artery running along the measurement site;

a pressing part that locally presses the areas corresponding to the first and second pulse wave sensors with respect to the circumferential direction of the first fluid bag from the outer circumference side of the first fluid bag, which is the other side of the inner circumference side where the first and second pulse wave sensors are mounted;

a first blood pressure calculation part that calculates blood pressure based on pulse transit time obtained from the outputs of the first and second pulse wave sensors, with the first fluid bag being in an unpressurized state, and the first and second pulse wave sensors being pressed by the pressing force of the pressing part; and, a second blood pressure calculation part that calculates blood pressure based on the pressure within the first fluid bag with the first fluid bag being in a pressurized state for oscillometric blood pressure measurement.

As used herein, the "measurement site" refers to a site along which an artery runs. The measurement site may be, for example, an upper limb, such as a wrist or an upper arm, or a lower limb, such as an ankle or a thigh.

Also, the "fluid bag" refers to a bag-shaped member capable of containing a fluid, whatever it may be called. For example, it may be called a "cuff" instead of a fluid bag. The "fluid" can contain both a liquid and a gas, and for example, water or air may be used.

The "width direction" of the fluid bag corresponds to the longitudinal direction of the measurement site.

BRIEF DESCRIPTION OF DRAWINGS

The present invention will become more fully understood from the detailed description given hereinbelow and the accompanying drawings which are given by way of illustration only, and thus are not limitative of the present invention, and wherein.

DESCRIPTION OF EMBODIMENT

Embodiments of the present invention will now be described in detail with reference to drawings.
(Structure of Sphygmomanometer)

Figure 1:
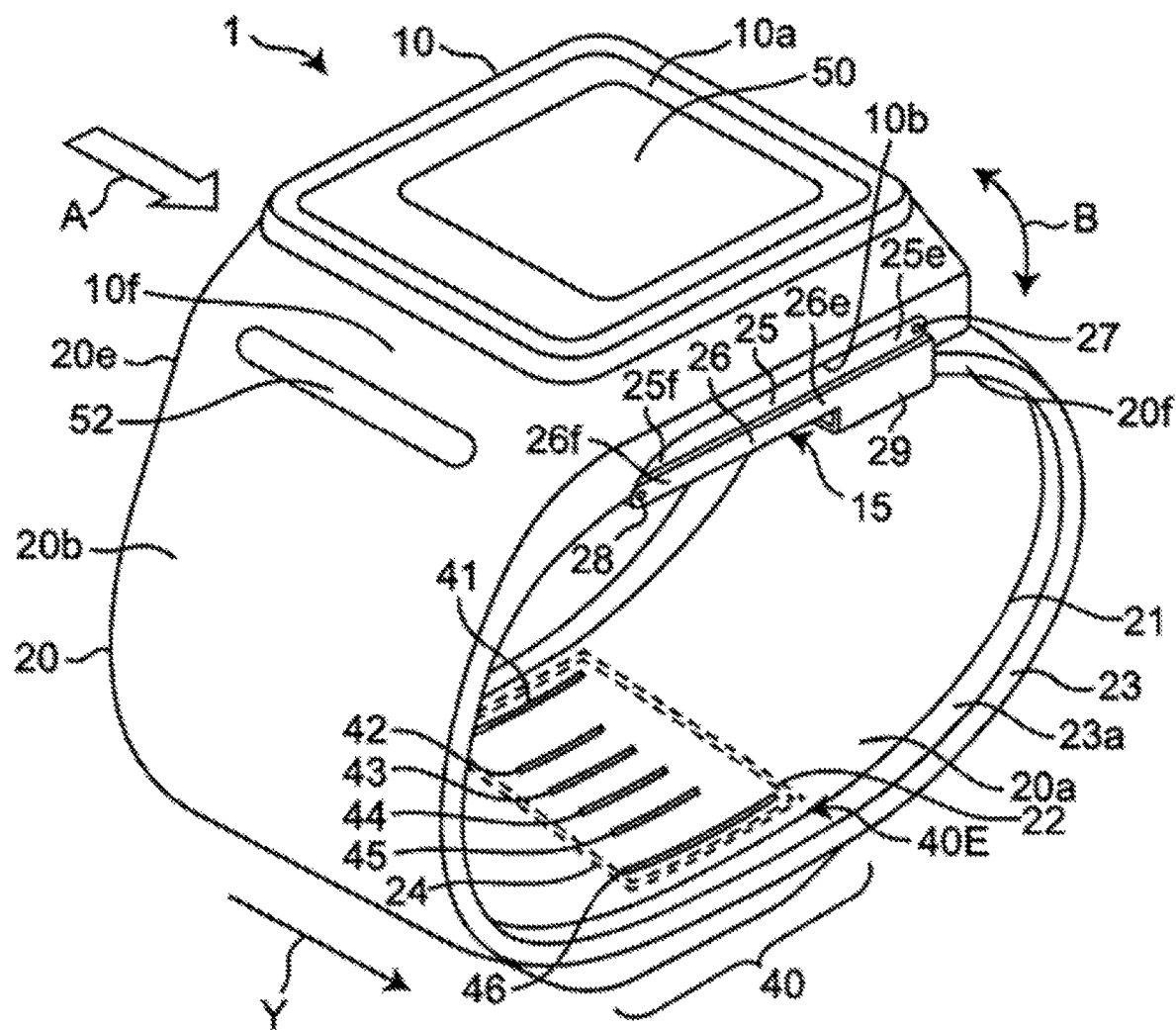
FIG. 1 is an external perspective view of a wrist-type sphygmomanometer according to an embodiment of the present invention.
Figure 2:
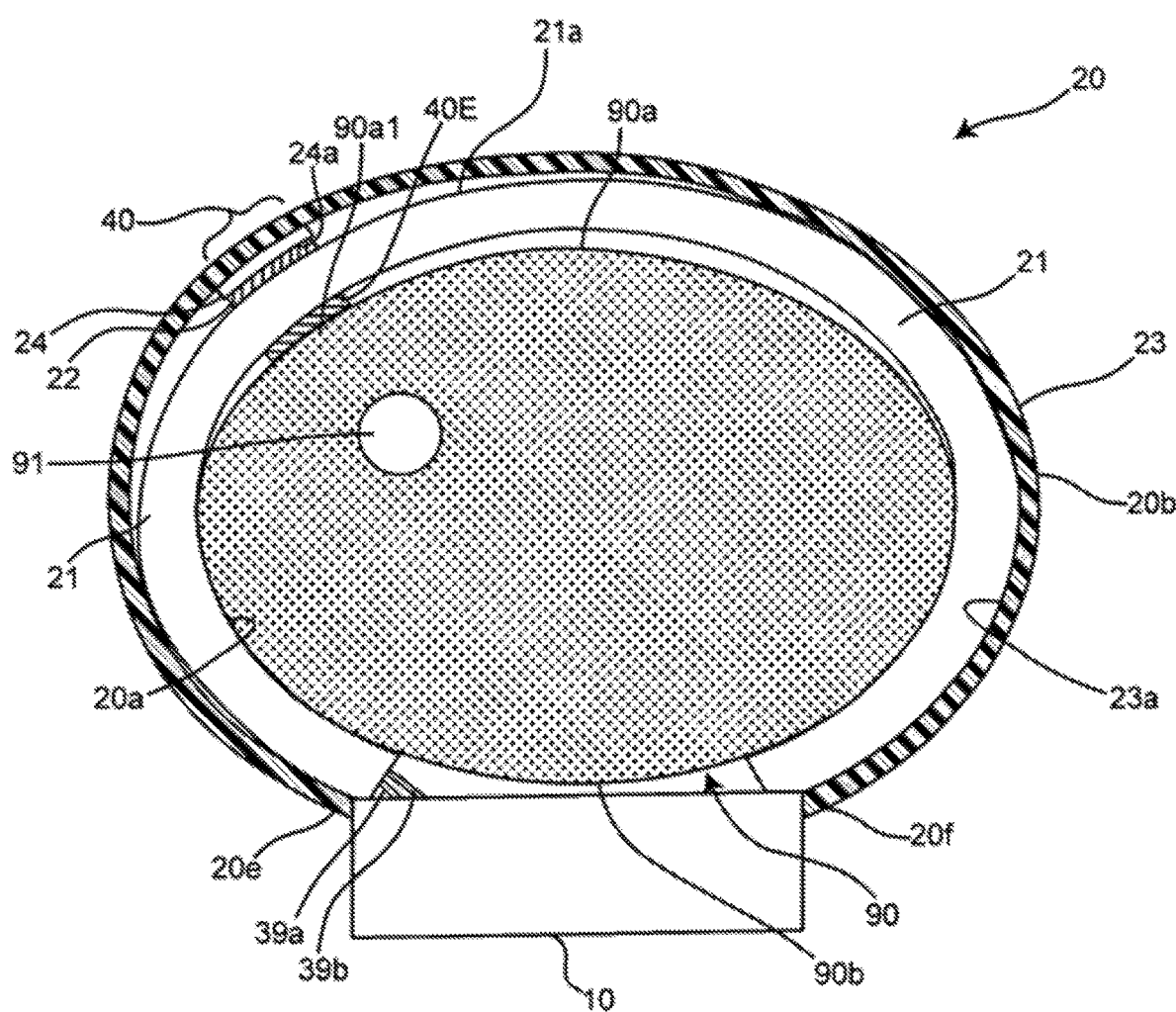
FIG. 2 is a schematic cross-sectional view perpendicular to the longitudinal direction of a left wrist with the sphygmomanometer being worn on the wrist.

FIG. 1 is an external perspective view of a wrist-type sphygmomanometer according to an embodiment (the entire sphygmomanometer is indicated with the reference number 1). FIG. 2 is a schematic cross-sectional view perpendicular to the longitudinal direction of a left wrist 90, which is a measurement site and around which the sphygmomanometer 1 is being worn (hereinafter referred to as "with the sphygmomanometer 1 being worn").

As shown in these drawings, the sphygmomanometer 1 mainly includes a belt 20 to be worn around the left wrist 90 of a user, and a main body 10 integrally attached to the belt 20.

As clear from FIG. 1, the belt 20 has an elongated strip-shape to be wrapped around the left wrist 90 in the circumferential direction. In this example, the belt 20 has a length in its width direction Y (width) of about 30 mm. The belt 20 includes a strip-shaped body 23 forming an outer circumferential surface 20b, and a pressure cuff 21 in the form of a first fluid bag provided along an inner circumferential surface 23a of the strip-shaped body 23 and forming an inner circumferential surface 20a to contact the left wrist 90 (refer to FIG. 2). In the same manner as the belt 20, the pressure cuff 21 has an elongated strip shape to be wrapped around the left wrist 90 in the circumferential direction.

The main body 10 is provided on an end portion 20e with respect to the circumferential direction of the belt 20, integrally with the belt 20 through, in this case, integral molding. The belt 20 and the main body 10 may be formed separately, and then the main body 10 may be attached integrally to the belt 20 with an engaging member (for example, a hinge). In this example, the main body 10 is to be arranged on a site corresponding to the back surface (the surface on the back of the hand) 90b of the left wrist 90 when the sphygmomanometer 1 is being worn (refer to FIG. 2). FIG. 2 shows a radial artery 91 running in the left wrist 90 near the palm-side surface (the surface on the palm side).

As clear from FIG. 1, the main body 10 has a three-dimensional shape having a thickness in the vertical direction relative to the outer circumferential surface 20b of the belt 20. The main body 10 is formed small and thin not to interfere with the user's daily activities. In this example, the main body 10 has a truncated pyramid profile protruding outward from the belt 20.

The main body 10 has a display 50, which serves as a display screen, on its top surface 10a (the surface farthest from the measurement site). The main body 10 also has an operation part 52 for inputting instructions from a user along a side surface 10f (the surface on the left front side in FIG. 1).

An impedance measurement part 40, which includes the first and second pulse wave sensors, is provided at a site on the belt 20 between the end portion 20e and another end portion 20f with respect to the circumferential direction and on the inner circumferential surface 20a of the pressure cuff 21, which constitutes the inner circumferential surface 20a of the belt 20. Six electrodes 41 to 46 in the form of a plate (or a sheet) (collectively referred to as a "group of electrodes" with the reference number 40E) are arranged on the belt 20 in a manner to be spaced from one another with respect to the width direction Y of the belt 20 on the inner circumferential surface 20a of the site where the impedance measurement part 40 is arranged (detailed later). In this example, the site on which the group of electrodes 40E is arranged faces the radial artery 91 of the left wrist 90 when the sphygmomanometer 1 is worn (refer to FIG. 2).

A solid 22 is arranged at a position corresponding to the group of electrodes 40E on an outer circumferential surface 21a, which is the other side of the inner circumferential surface 20a of the pressure cuff 21 where the group of electrodes 40E is arranged (refer to FIG. 2). Further, a press cuff 24, or a second fluid bag, is arranged on the outer circumference side of the solid 22. The press cuff 24, or the second fluid bag, serves as an expandable member for locally pressing an area corresponding to the group of electrodes 40E with respect to the circumferential direction of the pressure cuff 21. The press cuff 24 is arranged on the inner circumferential surface 23a of the strip-shaped body 23, which forms the belt 20 (refer to FIG. 2). The press cuff 24 is a fluid bag expandable and contractible in the thickness direction of the belt 20, and turns into a pressurized state or an unpressurized state by supply or discharge of fluid.

As shown in FIG. 1, a bottom surface 10b (the surface closest to the measurement site) of the main body 10 and the end portion 20f of the belt 20 are connected to each other with a three-fold buckle 15. The buckle 15 includes a first plate member 25 arranged on the outer circumference side, and a second plate member 26 arranged on the inner circumference side. The first plate member 25 has an end portion 25e pivotably attached to the main body 10 with a coupling rod 27 extending in width direction Y. The first plate member 25 has another end portion 25f pivotably attached to an end portion 26e of the second plate member 26 with a coupling rod 28 extending in width direction Y. The second plate member 26 has another end portion 26f fixed near the end portion 20f of the belt 20 with a fixing part 29. The position to which the fixing part 29 is attached with respect to the circumferential direction of the belt 20 is pre-adjusted to the length around the left wrist 90 of a user. Thus, the sphygmomanometer 1 (the belt 20) has a substantially ring shape in overall, and the bottom surface 10b of the main body 10 and the end portion 20f of belt 20 are openable or closable in the direction of an arrow B by means of the buckle 15.

To wear the sphygmomanometer 1 on the left wrist 90, the buckle 15 is opened to enlarge the diameter of the belt 20. In this state, the user passes his or her left hand through the belt 20 in the direction indicated by an arrow A in FIG. 1. As shown in FIG. 2, the user then adjusts the angular position of the belt 20 around the left wrist 90 to position the impedance measurement part 40 of the belt 20 above the radial artery 91 running through the left wrist 90. This allows the group of electrodes 40E of the impedance measurement part 40 to contact an area 90a1, which corresponds to the radial artery 91, in the palm side surface 90a of the left wrist 90. In this state, the user closes the buckle 15 to fix it. In this manner, a user wears the sphygmomanometer 1 (the belt 20) on his or her left wrist 90.

As shown in FIG. 2, in this example, the strip-shaped body 23 is formed from a plastic material that is flexible in the thickness direction, and is substantially nonelastic in the circumferential direction (longitudinal direction). In this example, the pressure cuff 21 is formed as a fluid bag by arranging two elastic polyurethane sheets to face each other in their thickness direction, and adhering their peripheral edges together. As described above, the group of electrodes 40E of the impedance measurement part 40 is arranged at the site corresponding to the radial artery 91 of the left wrist 90 on the inner circumferential surface 20a of the pressure cuff 21 (the belt 20).

Figure 3:
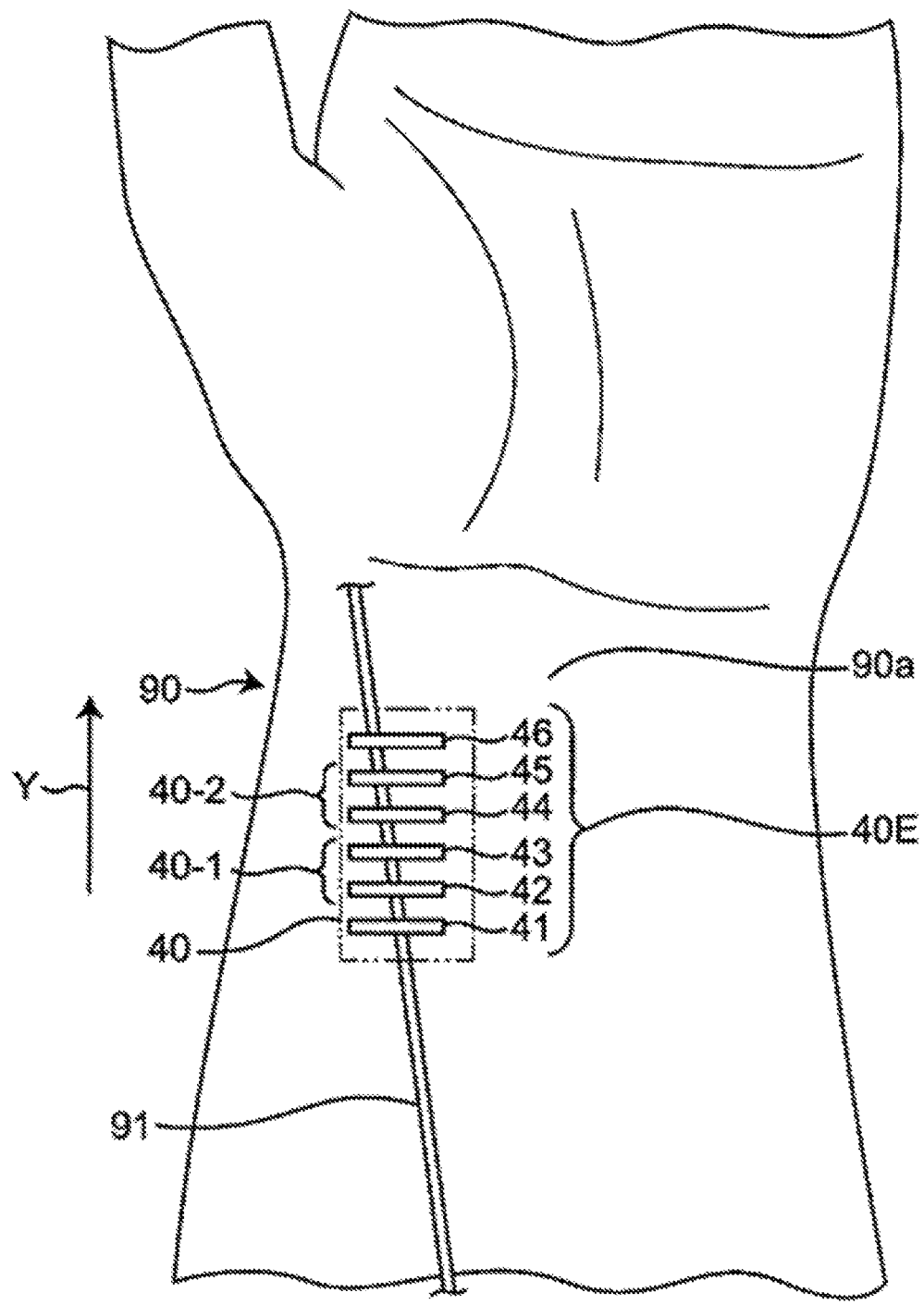
FIG. 3 is a planar layout of electrodes for impedance measurement, which constitute the first and second pulse wave sensors, with the sphygmomanometer being worn on a left wrist.

As shown in FIG. 3, when the sphygmomanometer 1 is being worn, the electrodes of the group of electrodes 40E of the impedance measurement part 40 are arranged side by side along the longitudinal direction of the wrist (corresponding to the width direction Y of the belt 20), each facing the radial artery 91 of the left wrist 90. The group of electrodes 40E includes a pair of current electrodes 41, 46 arranged on both sides for introducing electric current, and a first pair of detection electrodes 42, 43 constituting a first pulse wave sensor 40-1, and a second pair of detection electrodes 44, 45 constituting a second pulse wave sensor 40-2 for voltage detection. The second pair of detection electrodes 44, 45 is arranged corresponding to an area downstream of the blood flow of the radial artery 91 than the first pair of detection electrodes 42, 43. In this example, a distance D between the center of the first pair of detection electrodes 42, 43 and the center of the second pair of detection electrodes 44, 45 in width direction Y (refer to FIG. 5(A)) is set to 20 mm. The distance D is equal to the substantial space between the first pulse wave sensor 40-1 and the second pulse wave sensor 40-2. In this example, the space between the first pair of detection electrodes 42 and 43, and the space between the second pair of detection electrodes 44 and 45 are both set to 2 mm with respect to width direction Y.

The group of electrodes 40E can be formed flat. Thus, the sphygmomanometer 1 can have the entire belt 20 with a small thickness. The group of electrodes 40E thus formed can also be made flexible. Thus, the group of electrodes 40E does not hinder the pressure cuff 21 from pressing the left wrist 90, nor impair the accuracy of the oscillometric blood pressure measurement (later described).

As shown in FIG. 2, the press cuff 24, which is the expandable member, is arranged as described above on the inner circumferential surface 23a of the strip-shaped body 23 forming the belt 20. In this example, the press cuff 24 is formed as a fluid bag by arranging two elastic polyurethane sheets to face each other in their thickness direction, and adhering their peripheral edges together. The solid 22 is arranged at a position corresponding to the group of electrodes 40E on the inner circumferential surface 24a of the press cuff 24. In this example, the solid 22 is formed from a plate-shaped resin (in this example, polypropylene) with a thickness of about 1 to 2 mm. In the present embodiment, the belt 20, the press cuff 24, and the solid 22 are used as a pressing part.

Figure 4:
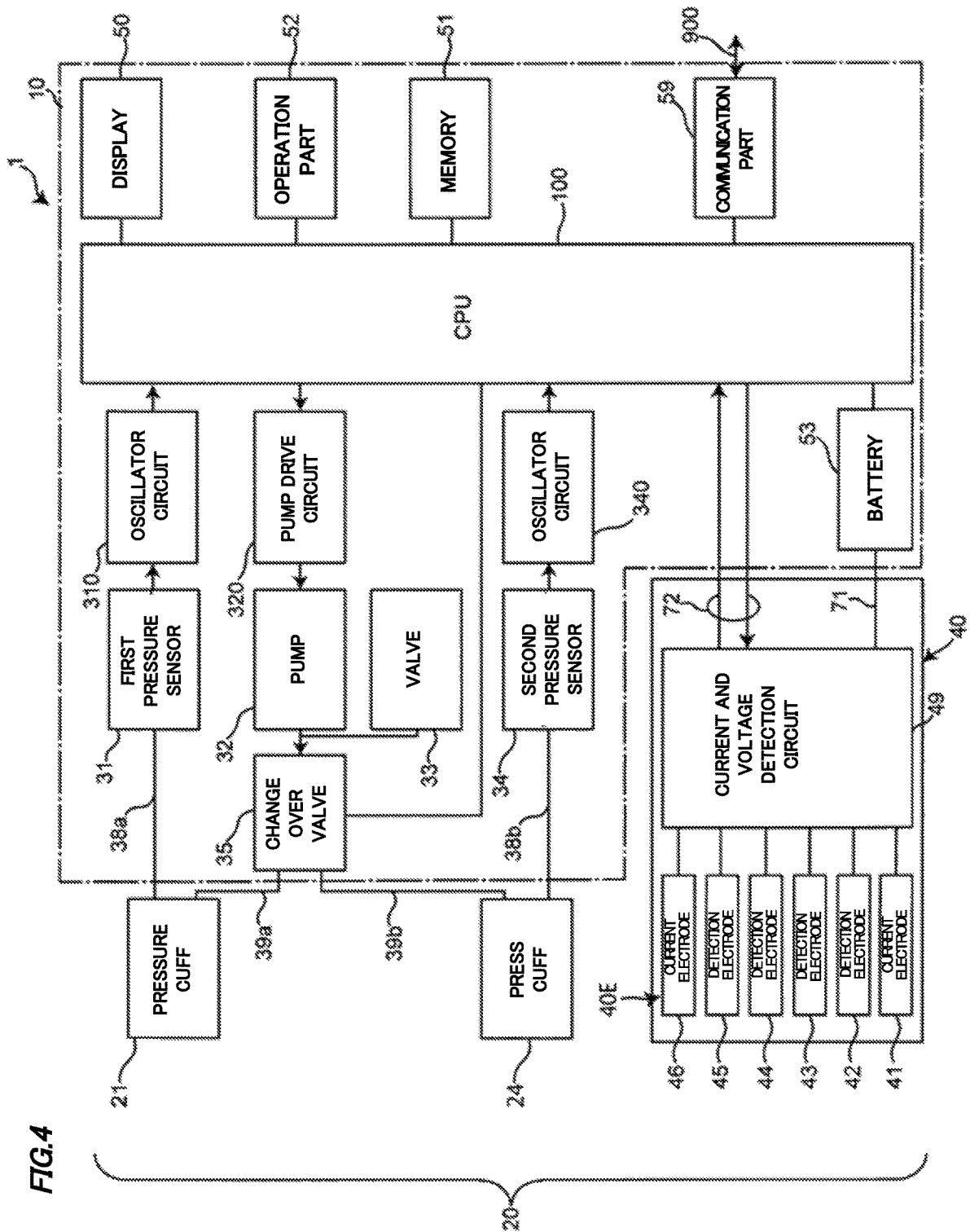
FIG. 4 is a block diagram of the control system of the sphygmomanometer.

FIG. 4 is a block diagram of the control system of the sphygmomanometer 1. The main body 10 of the sphygmomanometer 1 includes, in addition to the display 50 and the operation part 52 described above, a CPU (Central Processing Unit) 100 serving as a controlling part, a memory 51 serving as a storage part, and a communication part 59. The main body 10 includes the first pressure sensor 31, a pump 32, a valve 33, and the second pressure sensor 34. The main body 10 further includes an oscillator circuit 310 and an oscillator circuit 340 for respectively converting outputs from the first pressure sensor 31 and the second pressure sensor 34 into frequencies, and a pump drive circuit 320 for driving the pump 32. The impedance measurement part 40 includes, in addition to the group of electrodes 40E described above, a current and voltage detection circuit 49. A change-over valve 35 that changes the access point of the pump 32 and the valve 33 to the pressure cuff 21 or the press cuff 24, is also included.

In this example, the display 50 is an organic EL (electro luminescence) display, and displays information on blood pressure measurement including the results of blood pressure measurement and other information in accordance with control signals from the CPU 100. The display 50 is not limited to an organic EL display, and other types of displays, for example, an LCD (liquid crystal display) may be used.

In this example, the operation part 52 is a push type switch, from which operation signals corresponding to an instruction by a user to start or stop blood pressure measurement are input into the CPU 100. The operation part 52 is not limited to a push type switch, and may be, for example, a pressure-sensitive-type (resistive type) or proximity-type (electrostatic capacitance type) touch panel switch. Or, the sphygmomanometer 1 may include a micro-phone (not shown) through which a user may input an instruction with his or her voice to start blood pressure measurement.

The memory 51 nontemporarily stores, for example, program data for controlling the sphygmomanometer 1, data to be used for controlling the sphygmomanometer 1, data for setting various functions of the sphygmomanometer 1, and data of blood pressure measurement results. The memory 51 is also used as, for example, a work memory when a program is executed.

The CPU 100 executes various functions in accordance with programs for controlling the sphygmomanometer 1 stored in the memory 51. For example, to perform oscillometric blood pressure measurement, the CPU 100 performs, in response to the instruction from the operation part 52 to start blood pressure measurement, control of driving the pump 32 (and the valve 33) based on signals from the first pressure sensor 31. In this example, the CPU 100 also performs control of calculating a blood pressure level based on signals from the first pressure sensor 31.

When the CPU 100 executes pulse transit time-based blood pressure measurement, the CPU 100 performs control of driving the valve 33 to discharge air from the pressure cuff 21 in response to an instruction from the operation part 52 to start blood pressure measurement. The CPU 100 also drives the change-over valve 35 to change the access point of the pump 32 (and the valve 33) to the press cuff 24. The CPU 100 further performs control of calculating a blood pressure level based on signals from the second pressure sensor 34.

The communication part 59 is controlled by the CPU 100 to transmit prescribed information to an external device through a network 900, or receive information from an external device through the network 900 to transfer the information to the CPU 100. The communication through the network 900 may be by wireless or by wire. In the present embodiment, the network 900 is the Internet, but this is not limitative, and may be other networks, such as a LAN (Local Area Network) in a hospital, or one-to-one communication using a USB cable. The communication part 59 may include a micro USB connector.

The pump 32 and the valve 33 are connected to the pressure cuff 21 and the press cuff 24 through the change-over valve 35 and air pipes 39a, 39b. The first pressure sensor 31 is connected to the pressure cuff 21 through an air pipe 38a, and the second pressure sensor 34 is connected to the press cuff 24 through an air pipe 38b. The first pressure sensor 31 detects pressure within the pressure cuff 21 through the air pipe 38a. The change-over valve 35 is driven based on the control signals from the CPU 100, and changes the access point of the pump 32 and the valve 33 to the pressure cuff 21 or the press cuff 24. In this example, the pump 32 is a piezoelectric pump. When the access point of the pump 32 and the valve 33 has been changed to the pressure cuff 21 by the change-over valve 35, the pump 32 supplies air, which serves as a pressurizing fluid, to the pressure cuff 21 through the air pipe 39a to increase the pressure within the pressure cuff 21 (cuff pressure). When the access point of the pump 32 and the valve 33 has been changed to the pressure cuff 21 by the change-over valve 35, the pump 32 supplies air, which serves as a pressurizing fluid, to the press cuff 24 through the air pipe 39b to increase the pressure within the press cuff 24 (cuff pressure).

The valve 33 is mounted in the pump 32, and its opening or closing is controlled by on/off of the pump 32. In other words, when the access point of the pump 32 and the valve 33 has been changed to the pressure cuff 21 by the change-over valve 35, the valve 33 closes upon turning-on of the pump 32 to enclose air within the pressure cuff 21, whereas the valve 33 opens upon turning-off of the pump 32 to discharge air from the pressure cuff 21 to the atmosphere through the air pipe 39a. When the access point of the pump 32 and the valve 33 has been changed to the press cuff 24 by the change-over valve 35, the valve 33 closes upon turning-on of the pump 32 to enclose air within the press cuff 24, whereas the valve 33 opens upon turning-off of the pump the pump 32 to discharge the air from the press cuff 24 to the atmosphere through the air pipe 39b. The valve 33 also serves as a check valve, so that air to be discharged will never flow backward. The pump drive circuit 320 drives the pump 32 based on control signals sent from the CPU 100.

In this example, the first pressure sensor 31 is a piezoresistance type pressure sensor, and is connected to the pump 32, the valve 33, and the pressure cuff 21 through the air pipe 38a. The first pressure sensor 31 detects the pressure of the belt 20 (the pressure cuff 21) through the air pipe 38a with, in this example, the atmospheric pressure as a reference (zero), and outputs as time sequence signals. The oscillator circuit 310 oscillates in accordance with an electric signal value based on a change in electrical resistance caused by piezoresistance effect from the first pressure sensor 31, and outputs frequency signals with a frequency corresponding to electric signals of the first pressure sensor 31 to the CPU 100. In this example, the output of the first pressure sensor 31 is used to control the pressure of the pressure cuff 21, and to calculate blood pressure levels (including systolic blood pressure (SBP) and diastolic blood pressure (DBP)) by an oscillometric method.

When blood pressure is measured by a typical oscillometric method, the operation described below is usually carried out. Specifically, the cuff is wrapped around the measurement site (for example, an arm) of a subject beforehand. At the time of measurement, the CPU 100 controls the pump 32 and the valve 33 to increase the cuff pressure higher than highest blood pressure, and then to decrease gradually. During the pressure-decreasing process, the cuff pressure is detected by the pressure sensor, and fluctuations in artery volume of the artery of the measurement site are taken out as pulse wave signals. Maximum blood pressure (systolic blood pressure) and minimum blood pressure (diastolic blood pressure) are calculated based on changes in amplitude of the pulse wave signals (mainly the leading edge and the trailing edge) associated with changes in cuff pressure.

In this example, the second pressure sensor 34 is a piezoresistance type pressure sensor, and is connected to the pump 32, the valve 33, and the press cuff 24 through the air pipe 38b. The second pressure sensor 34 detects the pressure of the press cuff 24 through the air pipe 38b with, in this example, the atmospheric pressure as a reference (zero), and outputs as time sequence signals. The oscillator circuit 340 oscillates in accordance with an electric signal value based on a change in electrical resistance caused by piezoresistance effect from the second pressure sensor 34, and outputs frequency signals with a frequency corresponding to the electric signal of the second pressure sensor 34 to the CPU 100. In this example, the output of the second pressure sensor 34 is used to control the pressure of the press cuff 24, and to calculate pulse transit time-based blood pressure. To control the pressure of the press cuff 24 for pulse transit time-based blood pressure measurement, the CPU 100 controls the pump 32 and the valve 33 to increase or decrease cuff pressure in accordance with various conditions. The details will be described later.

A battery 53 supplies electric power to elements mounted on the main body 10. The battery 53 also supplies electric power to the current and voltage detection circuit 49 in the impedance measurement part 40 through a wire 71. The wire 71 is provided, together with a wire 72 for signals, between the strip-shaped body 23 and the pressure cuff 21 and extending between the main body 10 and the impedance measurement part 40 in the circumferential direction of the belt 20.

Figure 5A:
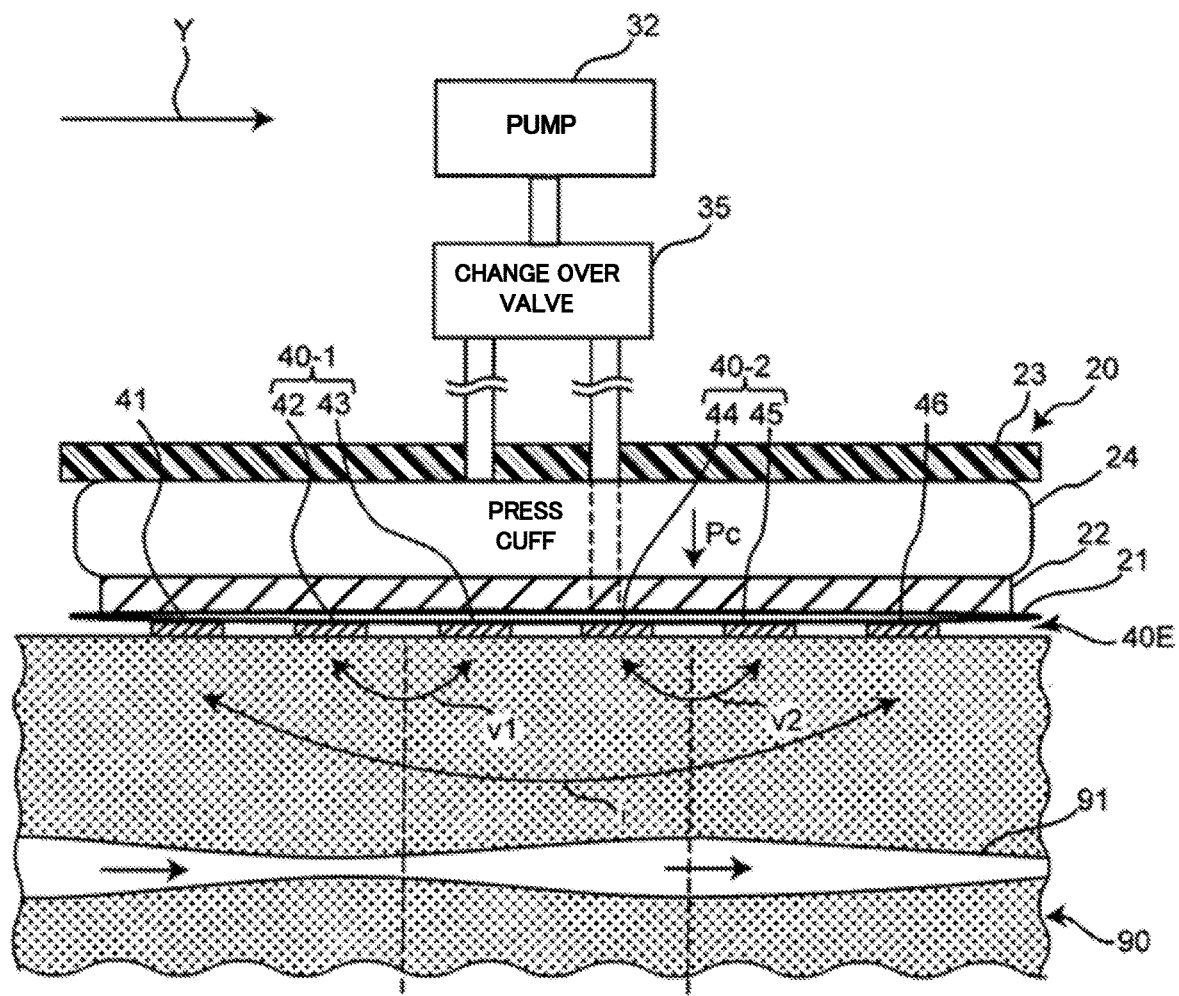
FIG. 5A is a schematic longitudinal cross-sectional view of a left wrist with the sphygmomanometer being worn on the wrist for pulse transit time-based blood pressure measurement.
Figure 5B:
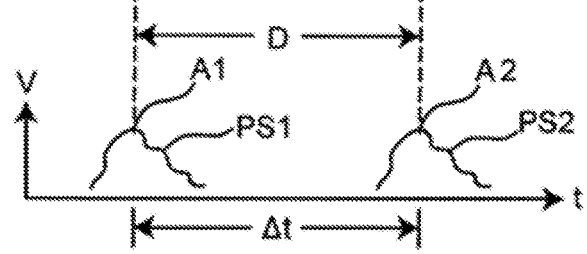
FIG. 5B is a graph showing the waveforms of the first and second pulse wave signals output from the first and second pulse wave sensors.

FIG. 5A is a schematic cross-sectional view in the longitudinal direction of the left wrist 90 with the sphygmomanometer 1 being wrapped around the wrist for pulse transit time-based blood pressure measurement. FIG. 5B shows waveforms of the first pulse wave signals PS1 and the second pulse wave signals PS2 output by the first pulse wave sensor 40-1 and the second pulse wave sensor 40-2 respectively. The current and voltage detection circuit 49 of the impedance measurement part 40 is controlled by the CPU 100, and, as shown in FIG. 5A, sends high-frequency constant current i, during its operation, with, in this example, a frequency of 50 kHz and a current value of 1 mA to the pair of current electrodes 41, 46 arranged on both sides with respect to the longitudinal direction of the wrist (corresponding to the width direction Y of the belt 20). In this state, the current and voltage detection circuit 49 detects voltage signals v1 between the first pair of detection electrodes 42, 43, which constitute the first pulse wave sensor 40-1, and voltage signals v2 between the second pair of detection electrodes 44, 45, which constitute the second pulse wave sensor 40-2. These voltage signals v1, v2 indicate changes in electric impedance (impedance method) by the pulse waves of blood current running through the area of the radial artery 91 corresponding to the first pulse wave sensor 40-1 and the second pulse wave sensor 40-2 in the palm side surface 90a of the left wrist 90. The current and voltage detection circuit 49 rectifies, amplifies, and filters these voltage signals v1, v2, and outputs the first pulse wave signals PS1 and the second pulse wave signals PS2 with mountain-shaped waveforms in time sequence as shown in FIG. 5B. In this example, the voltage signals v1, v2 are about 1 mV. Also, in this example, the first pulse wave signals PS1 and the second pulse wave signals PS2 have their respective peaks A1 and A2 of about 1 V.

Assuming that the blood flow of the radial artery 91 has a pulse wave velocity (PWV) in the range of 1000 cm/s to 2000 cm/s, the substantial distance between the first pulse wave sensor 40-1 and the second pulse wave sensor 40-2 is D=20 mm, and thus the time difference Δt between the first pulse wave signals PS1 and the second pulse wave signals PS2 is in the range of 1.0 ms to 2.0 ms.

As shown in FIG. 5A, the press cuff 24 is in a pressurized state, whereas the pressure cuff 21 from which air has been discharged is in an unpressurized state. The press cuff 24 is arranged over the first pulse wave sensor 40-1, the second pulse wave sensor 40-2, and the pair of current electrodes 41, 46 with respect to the artery direction of the radial artery 91. The solid 22 is also arranged over the first pulse wave sensor 40-1, the second pulse wave sensor 40-2, and the pair of current electrodes 41, 46 with respect to the artery direction of the radial artery 91. Thus, the press cuff 24 when pressurized by the pump 32 presses the first pulse wave sensor 40-1, the second pulse wave sensor 40-2, and the pair of current electrodes 41, 46 against the palm side surface 90a of the left wrist 90 via the solid 22. The respective pressing force of the pair of current electrodes 41, 46, the first pulse wave sensor 40-1, and the second pulse wave sensor 40-2 against the palm side surface 90a of the left wrist 90 can be set to an appropriate value. In the present embodiment, the press cuff 24 in the form of the fluid bag is used as a pressing part, so that the press cuff 24 can share the pump 32 and the valve 33 with the pressure cuff 21. This simplifies the structure. Further, the first pulse wave sensor 40-1, the second pulse wave sensor 40-2, and the pair of current electrodes 41, 46 being pressed via the solid 22 allows the pressing force against the measurement site to be uniform, and this enables accurate blood pressure measurement based on pulse transit time.

Figure 6:
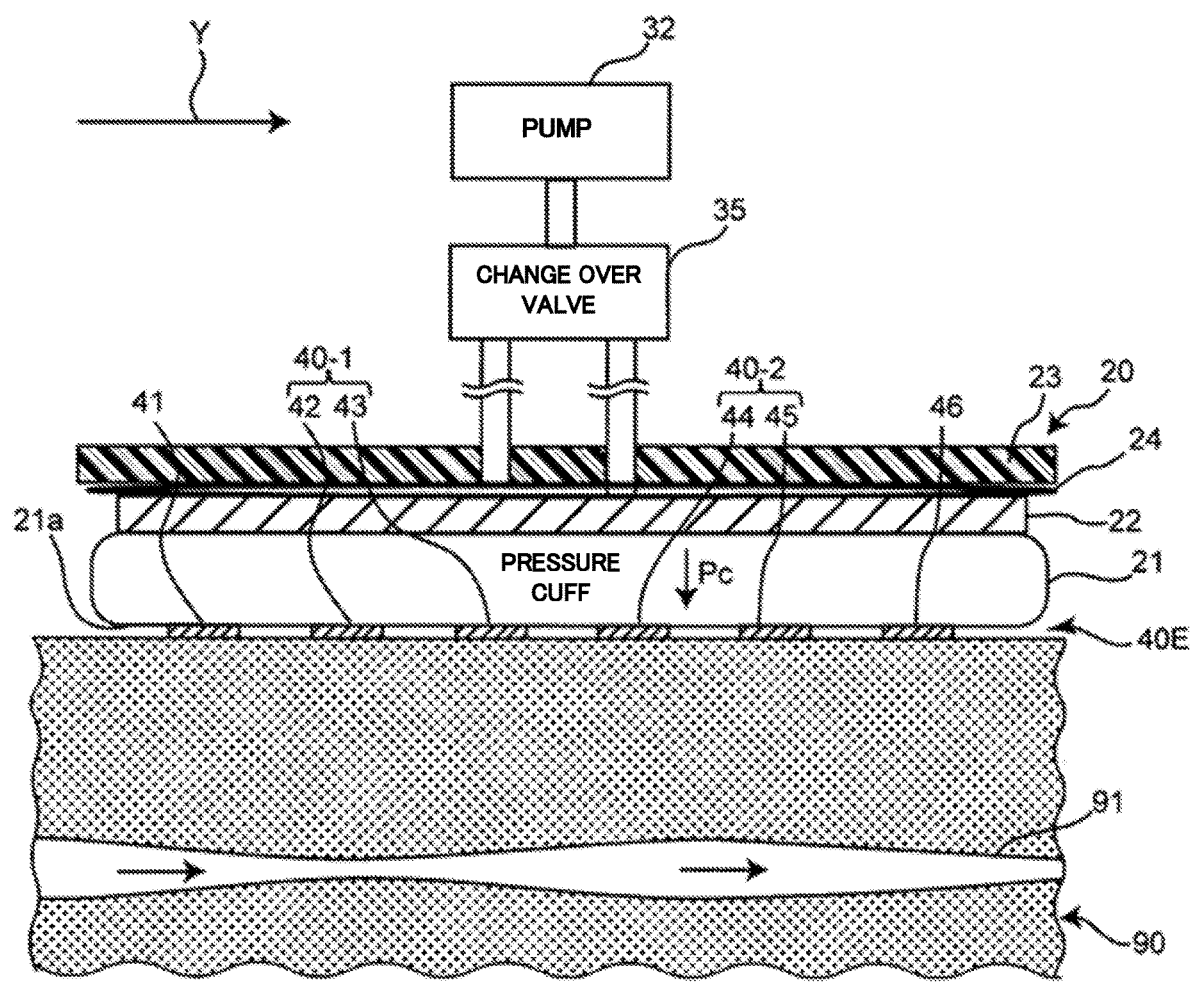
FIG. 6 is a schematic longitudinal cross-sectional view of a left wrist with the sphygmomanometer being worn around the wrist for oscillometric blood pressure measurement.

FIG. 6 is a schematic cross-sectional view in the longitudinal direction of the left wrist 90 with the sphygmomanometer 1 being wrapped around the wrist for oscillometric blood pressure measurement. In this case, the press cuff 24 from which air has been discharged is in an unpressurized state, whereas the pressure cuff 21 to which air has been supplied is in a pressurized state. When the pressure cuff 21, which extends in the circumferential direction of the wrist 90, is pressurized by the pump 32, the pressure cuff 21 equally presses the wrist 90 in the circumferential direction. Only the group of electrodes 40E is present between the inner circumferential surface of the pressure cuff 21 and the wrist 90. Thus, pressing by the pressure cuff 21 can sufficiently close the blood vessel without hindered by any other member. This enables accurate oscillometric blood pressure measurement.

(Operation of Oscillometric Blood Pressure Measurement)

Figure 7:
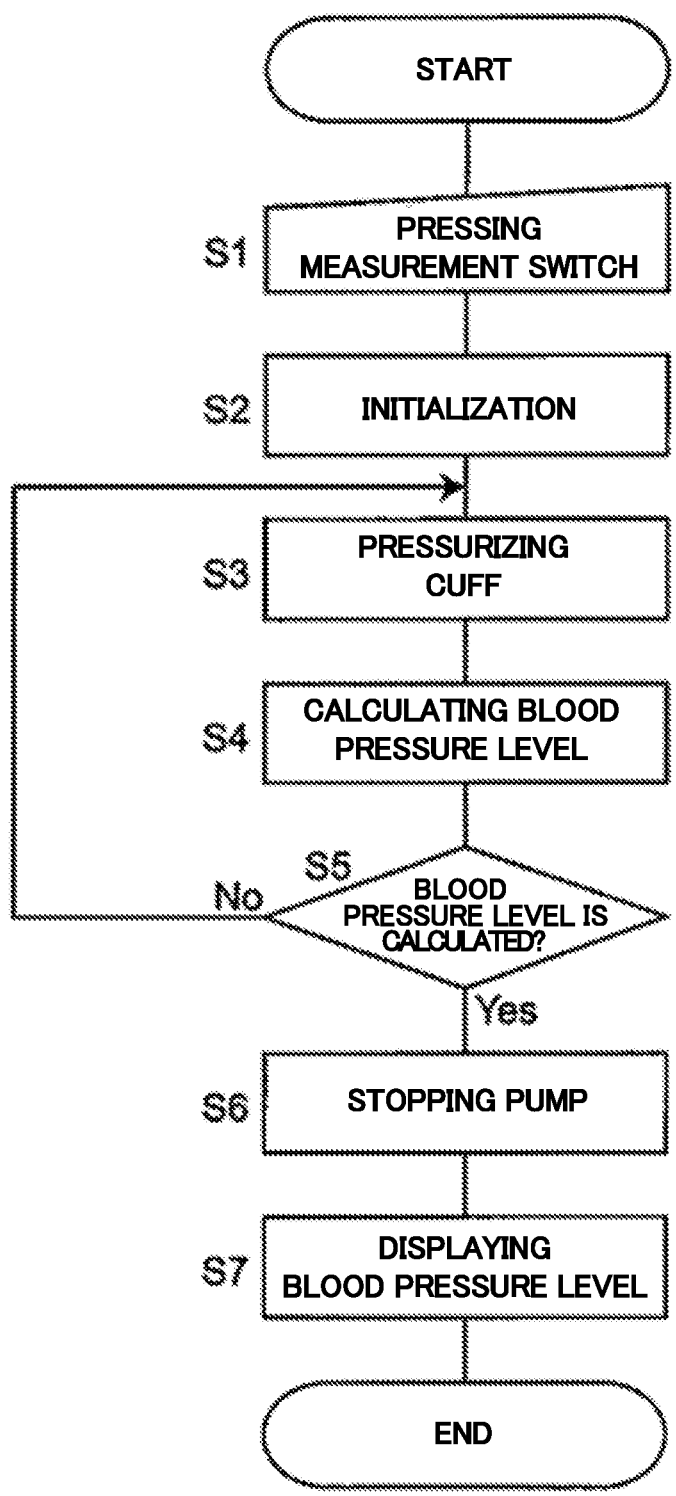
FIG. 7 is an operation flowchart of the sphygmomanometer 1 in performing oscillometric blood pressure measurement using the blood pressure measurement method according to an embodiment.

FIG. 7 is an operation flowchart of the sphygmomanometer 1 in performing oscillometric blood pressure measurement using a blood pressure measurement method according to an embodiment.

When a user instructs oscillometric blood pressure measurement through the operation part 52 in the form of a push type switch provided on the main body 10 (Step S1), the CPU 100 starts operation, and initializes the memory area for processing (Step S2). Also, the CPU 100 turns off the pump 32 via the pump drive circuit 320, and opens the valve 33 to discharge air from the pressure cuff 21. The CPU 100 then performs control of setting the current output value of the first pressure sensor 31 to a value equal to the atmospheric pressure (0 mmHg adjustment).

The CPU 100 then performs control of closing the valve 33, and then driving the pump 32 via the pump drive circuit 320 to send air to the pressure cuff 21. This expands the pressure cuff 21, and gradually increases the cuff pressure Pc (refer to FIG. 8) (Step S3 of FIG. 7).

Figure 8:
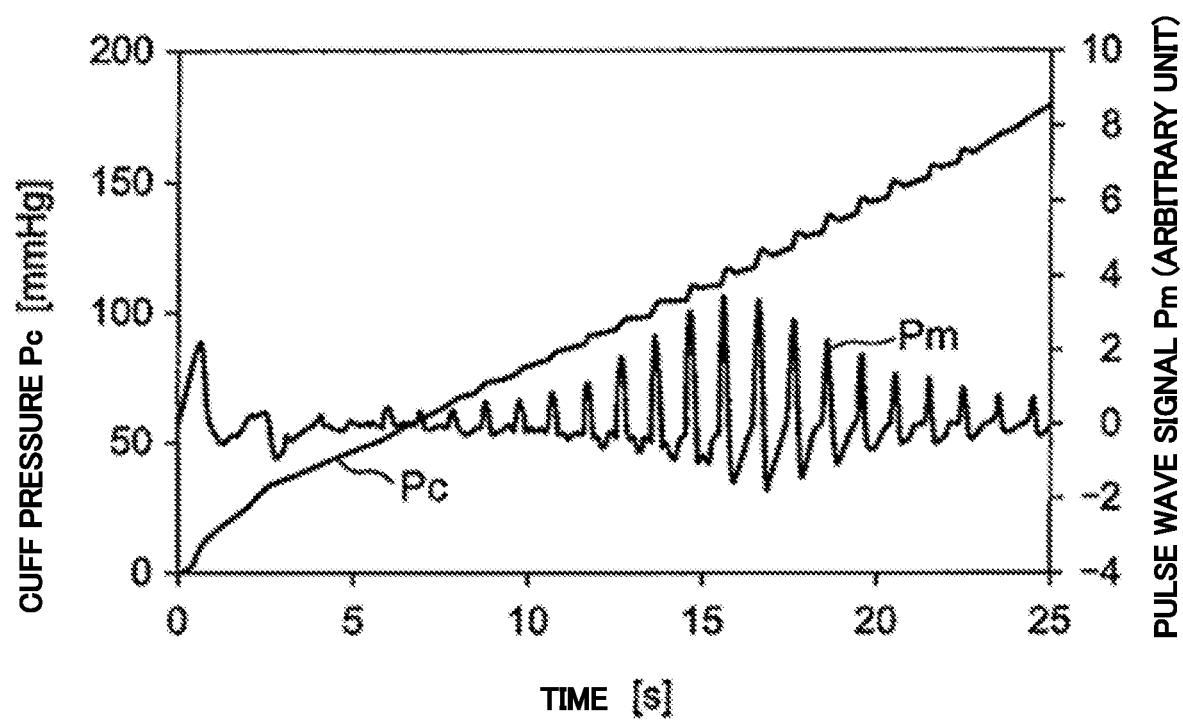
FIG. 8 is a graph showing changes in cuff pressure and pulse wave signals in accordance with the operation flowchart of FIG. 7.

During the pressurizing process, to calculate a blood pressure level, the CPU 100 monitors the cuff pressure Pc with the first pressure sensor 31, and acquires artery volume fluctuation components generated in the radial artery 91 of the left wrist 90, or the measurement site, as pulse wave signals Pm as shown in FIG. 8.

In Step S4 of FIG. 7, the CPU 100 then functions as a second blood pressure calculation part, and attempts to calculate blood pressure levels (systolic blood pressure (SBP) and diastolic blood pressure (DBP)) based on pulse wave signals Pm having been acquired by applying a known algorithm using an oscillometric method.

If calculation of blood pressure levels fails because of lack of data at this point (NO in Step S5), the processes in Steps S3 to S5 are repeated until the cuff pressure Pc reaches its upper limit pressure (which is predetermined to, for example, 300 mmHg, for safety).

When blood pressure levels are calculated in this manner (YES in Step S5), the CPU 100 stops the pump 32 through the pump drive circuit 320, and performs control of opening the valve 33 to discharge air from the pressure cuff 21 (Step S6). In the final step, the measurement results of blood pressure levels are displayed on the display 50, and recorded in the memory 51 (Step S7).

Calculation of blood pressure levels may be performed not only in the process of increasing the pressure but in the process of decreasing the pressure.

(Operation of Pulse Wave Propagation Time-Based Blood Pressure Measurement)

Figure 9:
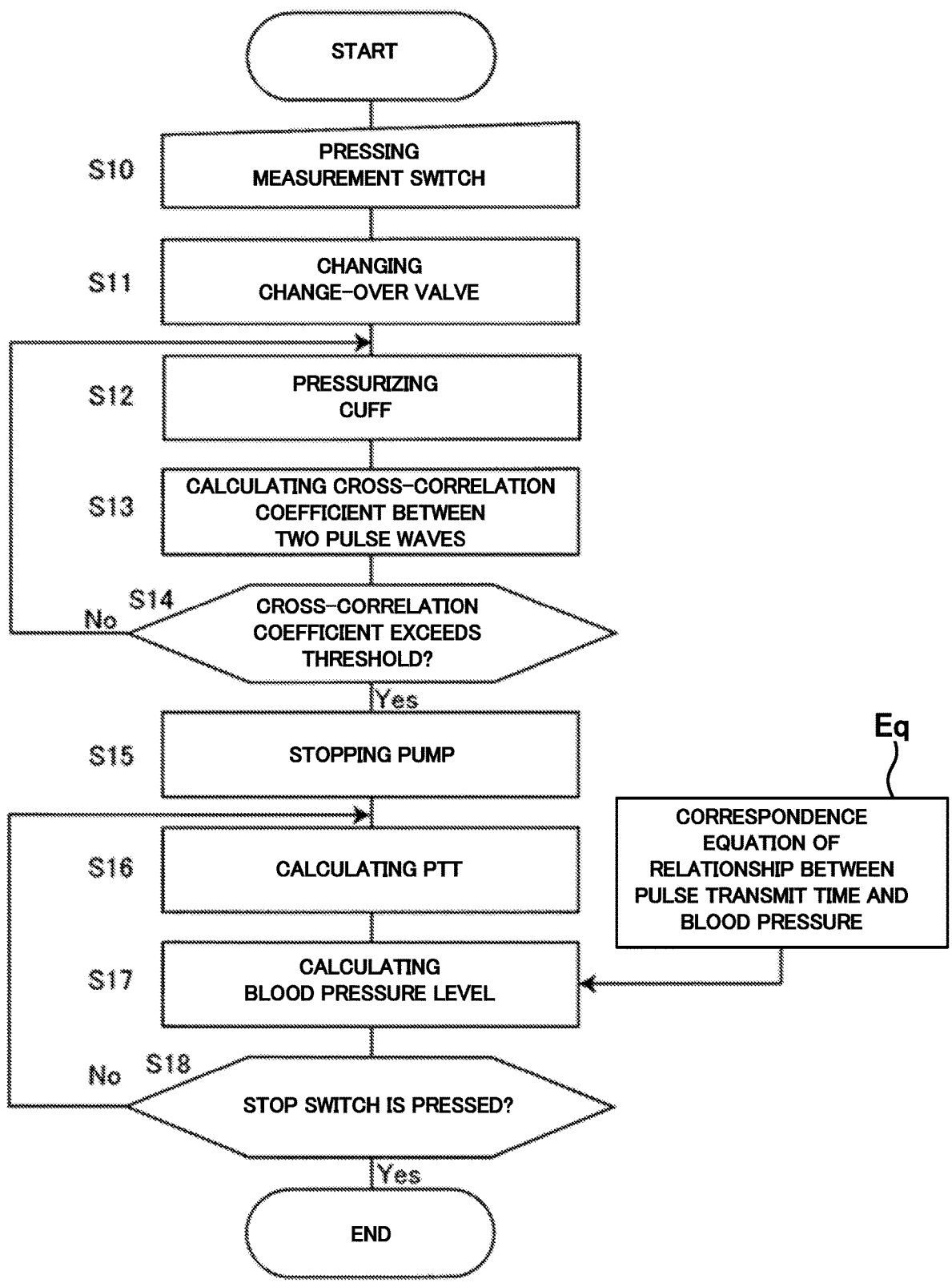
FIG. 9 is an operation flowchart of the sphygmomanometer in implementing the method for blood pressure measurement according to an embodiment, including obtaining pulse transit time (PTT) and performing blood pressure measurement (estimation) based on the pulse transit time.

FIG. 9 is an operation flowchart of the sphygmomanometer 1 in implementing a blood pressure measurement method according to an embodiment, including acquiring pulse transit time (PTT), and performing blood pressure measurement (estimation) based on the pulse transit time.

Figure 10:
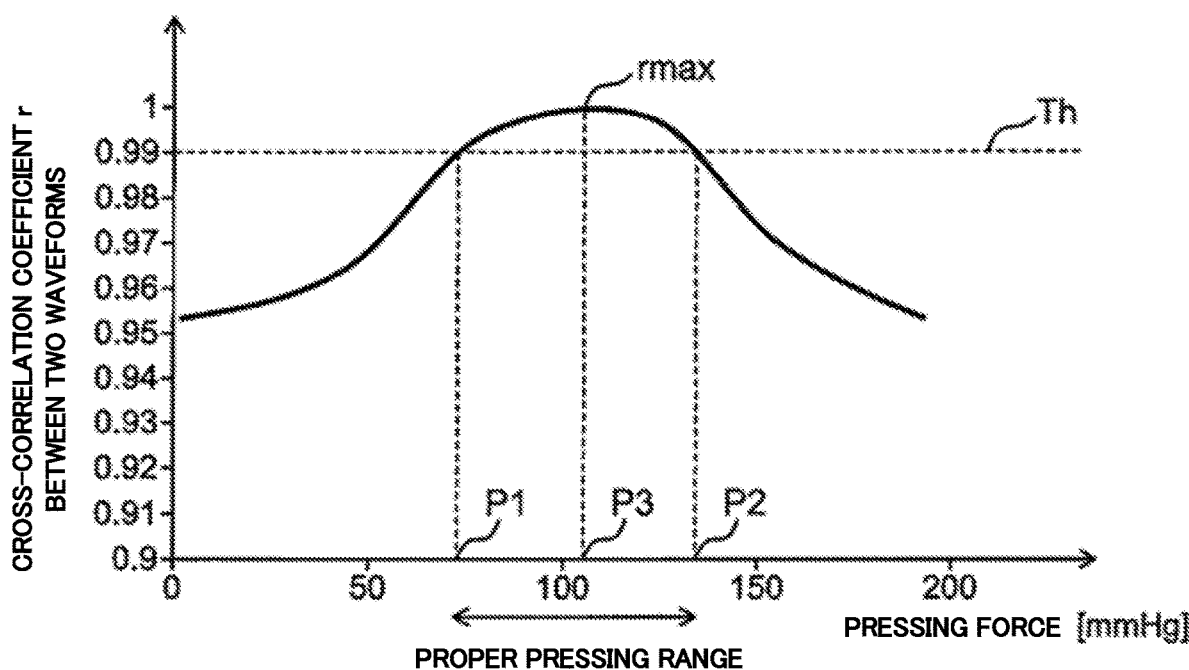
FIG. 10 is a graph showing a relationship between a pressing force against the pairs of detection electrodes and a cross-correlation coefficient between the waveforms of the first and second pulse wave signals output from the first and second pulse wave sensors.

The operation flowchart is created based on experimental results by the present inventors. Specifically, as shown in FIG. 10, the present inventors discovered through experiments that as the pressing force (equal to the cuff pressure Pc by the press cuff 24) of the first pulse wave sensor 40-1 (including the first pair of detection electrodes 42, 43) and the second pulse wave sensor 40-2 (including the second pair of detection electrodes 44, 45) against the left wrist 90, or the measurement site, gradually increases from zero, the cross-correlation coefficient r between the waveforms of the first and second pulse wave signals PS1, PS2 gradually increases until it indicates a maximum value, rmax, and then gradually decreases. The operation flowchart is based on the understanding that the range where the cross-correlation coefficient r exceeds a predetermined threshold Th (in this example, Th=0.99) is a proper range (which is referred to as "proper pressing range") of the pressing force. In this example, the proper pressing range of the pressing force (cuff pressure Pc) is from the lower limit P1=72 mmHg to the upper limit P2≈135 mmHg.

When a user instructs PTT-based blood pressure measurement through the operation part 52 in the form of a push type switch on the main body 10 (Step S10 of FIG. 9), the CPU 100 drives the change-over valve 35 to change the access point of the pump 32 and the valve 33 to the press cuff 24 (Step S11 of FIG. 8). The CPU 100 then performs control of closing the valve 33 and driving the pump 32 through the pump drive circuit 320 to send air to the press cuff 24. This expands the press cuff 24, and gradually increases the cuff pressure Pc (refer to FIG. 5(A)) (Step S12 of FIG. 9). In this example, the cuff pressure Pc is continuously increased at a constant rate (=5 mmHg/s). The cuff pressure Pc may be increased in stages to easily secure the time for calculating a cross-correlation coefficient described below.

During the pressurizing process, the CPU 100 serves as a cross-correlation coefficient calculation part, and acquires the first and second pulse wave signals PS1, PS2 respectively output in time sequence from the first pulse wave sensor 40-1 and the second pulse wave sensor 40-2 to calculate a cross-correlation coefficient r between the first and second pulse wave signals PS1, PS2 in real time (Step S13 of FIG. 9).

At the same time, the CPU 100 serves as a pressing force setting part, and determines whether the calculated cross-correlation coefficient r exceeds the predetermined threshold Th (=0.99) (Step S14 of FIG. 8). If the cross-correlation coefficient r is lower than or equal to the threshold Th (NO in Step S14 of FIG. 9), the processes of Steps S12 to S14 are repeated until the cross-correlation coefficient r exceeds the threshold Th. When the cross-correlation coefficient r exceeds the threshold Th (YES in Step S14 of FIG. 9), the CPU 100 stops the pump 32 (Step S15 of FIG. 9), and sets the cuff pressure Pc to the value at that time, or specifically at the time when the cross-correlation coefficient r exceeds the threshold Th. In this example, the cuff pressure Pc is set to the value when the cross-correlation coefficient r exceeded the threshold Th, specifically, P1 (≈72 mmHg) in FIG. 10.

In this state, the CPU 100 acquires the time difference Δt between the first and second pulse wave signals PS1, PS2 (refer to FIG. 5(B)) as a pulse transit time (PTT) (Step S16 of FIG. 9). More specifically, in this example, the time difference Δt between a peak A1 of the first pulse wave signals PS1 and a peak A2 of second pulse wave signals PS2 is acquired as a pulse transit time (PTT).

In this manner, the measurement accuracy of pulse transit time can be enhanced. The cuff pressure Pc being set to a value at the point of time when the cross-correlation coefficient r exceeds the threshold Th enables acquisition of a pulse transit time without increasing the cuff pressure Pc more than necessary. This can reduce the physical burden on a user.

The CPU 100 then serves as a first blood pressure calculation part, and calculates blood pressure (estimation) based on the pulse transit time (PTT) acquired in Step S16 using a predetermined equation Eq between pulse transit time and blood pressure (Step S17 of FIG. 9). The predetermined equation Eq between pulse transit time and blood pressure is provided as, for example, a known fractional function including the term $1/DT^2$ as shown in the equation (Eq. 2) in FIG. 13 where DT denotes a pulse transit time, and EBP denotes blood pressure (refer to, for example, Japanese Patent Application Publication No. Hei 10-201724). In the equation (Eq. 2), α and β denote a known coefficient and a constant respectively.

The enhanced accuracy in measurement of pulse transit time described previously can enhance accuracy in calculation of blood pressure (estimation) performed in this manner. The measurement results of blood pressure levels are displayed on the display 50 and recorded in the memory 51.

In this example, in Step S18 of FIG. 9, unless measurement stop is instructed through the operation part 52 in the form of a push type switch (No in Step S18 of FIG. 8), calculation of a pulse transit time (PTT) (Step S16 of FIG. 9) and calculation of blood pressure (estimation) (Step S17 of FIG. 9) are periodically repeated for each input of first and second pulse wave signals PS1, PS2 corresponding to pulse waves. The CPU 100 displays renewed measurement results of a blood pressure level on the display 50, and stores and records in the memory 51. When stop of measurement is instructed in Step S18 of FIG. 9 (YES in Step S18 of FIG. 9), measurement operation is terminated.

The sphygmomanometer 1 enables continuous measurement of PTT-based blood pressure for a long time with a less physical burden on a user.

Also, the sphygmomanometer 1 enables measurement of both PTT blood pressure (estimation) and oscillometric blood pressure with a single device. This is highly convenient for a user.

(Verification of Effects of Setting Pressing Force)

Figure 11A:
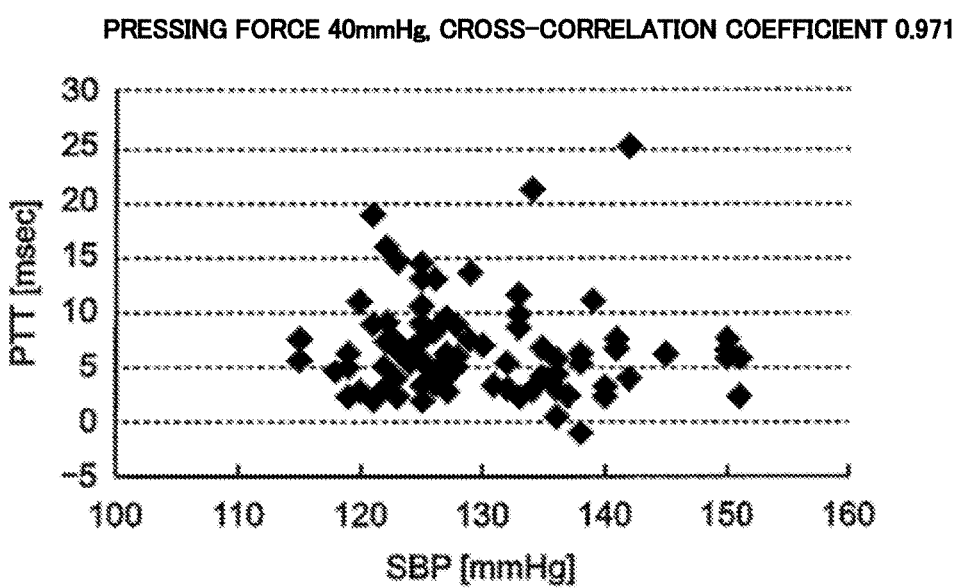
FIG. 11A is a scattergram showing the relationship between pulse wave propagation times (PTT) obtained under the condition of a pressing force (cuff pressure Pc) of 40 mmHg (which is lower than the lower limit P1 of FIG. 10) and systolic blood pressures (SBP) obtained by oscillometric blood pressure measurement of various users (subjects) using the sphygmomanometer.

The scattergram of FIG. 11A shows the relationship between pulse transit times (PTT) obtained under the condition of a pressing force (cuff pressure Pc) of 40 mmHg (which is lower than the lower limit P1 of FIG. 10) and systolic blood pressures (SBP) obtained by oscillometric blood pressure measurement of various users (subjects) using the sphygmomanometer 1 (Step S5 of FIG. 7). Under this pressing force setting condition, the cross-correlation coefficient r between the waveforms of the first and second pulse wave signals PS1, PS2 was r=0.971, which was lower than the threshold Th (=0.99). As clear from FIG. 11A, there is substantially no correlation between the pulse transit times (PTT) and the systolic blood pressures (SBP). The correlation coefficient calculated through fitting the equation of FIG. 3 (Eq. 2) was −0.07.

Figures 11B, 12, 13, 14, 15:
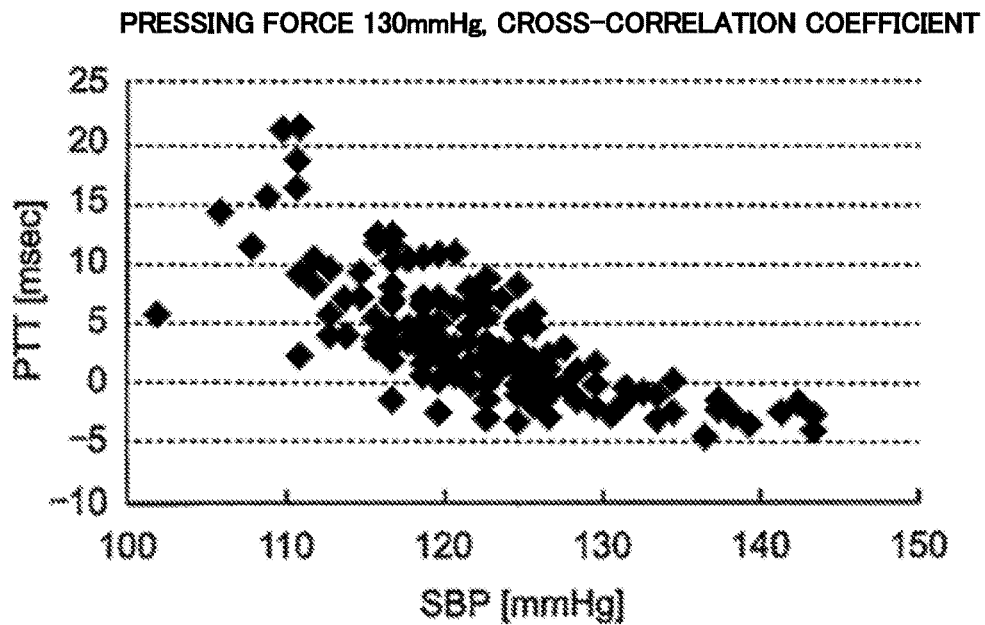
FIG. 11B is a scattergram showing the relationship between pulse wave propagation times (PTT) obtained under the condition of a pressing force (cuff pressure Pc) of 130 mmHg (which falls within the proper pressing range between the lower limit P1 and the upper limit P2 in FIG. 10) and systolic blood pressures (SBP) obtained by oscillometric blood pressure measurement of various users (subjects) using the sphygmomanometer.
FIG. 12 is an example equation showing a cross-correlation coefficient r between data sequence $\{x_i\}$ and data sequence $\{y_i\}$.
FIG. 13 is an example of a predetermined correspondence equation of the relationship between pulse transit time and blood pressure.
FIG. 14 is another example of a predetermined correspondence equation of the relationship between pulse transit time and blood pressure.
FIG. 15 is yet another example of a predetermined correspondence equation of the relationship between pulse transit time and blood pressure.

In contrast, the scattergram of FIG. 11B shows the relationship between pulse transit times (PTT) obtained under the condition of a pressing force (cuff pressure Pc) of 130 mmHg (which falls within the proper pressing range between the lower limit P1 and the upper limit P2 in FIG. 10) and systolic blood pressures (SBP) obtained by oscillometric blood pressure measurement of various users (subjects) using the sphygmomanometer 1 (Step S5 of FIG. 7). Under the pressing force setting condition, the cross-correlation coefficient r between the waveforms of the first and second pulse wave signals PS1, PS2 was r=0.9901, exceeding the threshold Th (=0.99). As clear from FIG. 11B, there is a strong correlation between the pulse transit times (PTT) and the systolic blood pressures (SBP). The correlation coefficient calculated through fitting the equation of FIG. 3 (Eq. 2) was −0.90.

The results of FIGS. 11A and 11B demonstrated that obtaining a pulse transit time (PTT) by setting a pressing force (cuff pressure Pc) to a value where the cross-correlation coefficient r exceeds the threshold Th (=0.99) can enhance the correlation between pulse transit time (PTT) and systolic blood pressure (SBP). The reason why the correlation between the pulse transit time (PTT) and the systolic blood pressure (SBP) was increased is that setting of a pressing force according to the present invention is believed to have enhanced measurement accuracy of pulse transit time (PTT). This can increase measurement accuracy of blood pressure.

MODIFIED EXAMPLES

In the embodiment described above, the equation (Eq. 2) of FIG. 13 was used in Step S17 of FIG. 9 as a correspondence equation between pulse transit time and blood pressure to calculate blood pressure (estimation) based on pulse transit time (PTT). However, this is not limitative. As a correspondence equation Eq between pulse transit time and blood pressure, as shown, for example, in the equation of FIG. 14 (Eq. 3), an equation containing the term of 1/DT and the term of DT in addition to the term of $1/DT^2$ may be used where D1 denotes pulse transit time and EBP denotes blood pressure. In the equation (Eq. 3), $\alpha$, $\beta$, $\gamma$, and $\Delta$ each denote a known coefficient or a constant.

Further, for example, as shown in the equation (Eq. 4) of FIG. 15, an equation containing the term of 1/DT, the term of cardiac cycle RR, and the term of volume pulse wave area ratio VR may be used (refer to, for example, Japanese Patent Application Publication No. 2000-3307). In the equation (Eq. 4), $\alpha$, $\beta$, $\gamma$, and $\Delta$ each denote a known coefficient or a constant. In this case, the CPU 100 calculates a cardiac cycle RR and a volume-pulse-wave area ratio VR based on pulse wave signals PS1, PS2.

When these equations (Eq. 3 and Eq. 4) are used as a correspondence equation Eq between pulse transit time and blood pressure, the measurement accuracy of blood pressure can also be enhanced in the same manner as in the case where the equation (Eq. 2) is used. Of course, other correspondence equations may be used in addition to the equations (Eq. 2, Eq. 3, and Eq. 4).

In the embodiment described above, the first pulse wave sensor 40-1 and the second pulse wave sensor 40-2 detect pulse waves passing through the artery (radial artery 91) along the measurement site (the left wrist 90) as changes in impedance (impedance method). However, this is not limitative. The first and second pulse wave sensors each may include a light emitting element that emits light toward the artery running along the corresponding area of the measurement site, and a light receiving element that receives its reflected light (or transmitted light) to detect pulse waves of the artery as changes in volume (photoelectric method). Or, the first and second pulse wave sensors each may include a piezoelectric sensor contacting the measurement site to detect a distortion by the pressure of the corresponding area of the artery running along the measurement site as an electrical change (piezoelectric method). Further, the first and second pulse wave sensors each may include a transmission element that sends radio wave (transmission wave) toward the artery running along the corresponding area of the measurement site, and a receiving element that receives reflected waves of the radio wave to detect changes in distance between the artery and the sensors caused by the pulse waves of the artery as a phase shift between the transmission wave and the reflected wave (radio wave radiation method).

In the embodiment described above, the sphygmomanometer 1 is expected to be worn around the left wrist 90 or the measurement site. However, this is not limitative. The measurement site may be, for example, an upper limb, such as an upper arm other than a wrist, or a lower limb, such as an ankle or a thigh along which an artery runs.

The embodiment described above cited the belt 20, the press cuff 24, and the solid 22 as an example of the pressing part. However, the present invention is not limited to this example. The pressing part may be a pressing part mechanically expandable in the thickness direction to press the first pulse wave sensor 40-1 and the second pulse wave sensor 40-2 from the circumferential surface of the pressure cuff 21 in an unpressurized state. Also, the embodiment described above cited the press cuff 24 in the form of a fluid bag as an example of the expandable member. However, the present invention is not limited to this example. An expandable member mechanically expandable in the thickness direction may be used to press the first pulse wave sensor 40-1 and the second pulse wave sensor 40-2 through the solid 22.

Also, in the embodiment described above, the CPU 100 mounted in the sphygmomanometer 1 serves as a cross-correlation coefficient calculation part, a pressing force setting part, and a first and second blood pressure calculation part to perform oscillometric blood pressure measurement (the operation flowchart of FIG. 7) and PTT-based blood pressure measurement (estimation) (the operation flowchart of FIG. 9). However, this is not limitative. For example, an essential computer device, such as a smart phone, provided outside the sphygmomanometer 1 may serve as a waveform comparison part, a part for setting pulse wave sensor pressing force, a part for setting current and electrode pressing force, a measurement processing part, and a first and second blood pressure calculation part to order the sphygmomanometer 1 to perform oscillometric blood pressure measurement (the operation flowchart of FIG. 7) and PTT-based blood pressure measurement (estimation) (the operation flowchart of FIG. 9) through the network 900.

In the embodiment described above, the main body 10 including the pump 30 is integrally formed with the belt 20. However, the present invention is not limited to this example. The sphygmomanometer 1 may include the pressure cuff 21 including the belt 20 and the press cuff 24, and a desk-top main body, and a pump may be included in the main body. In this case, the cuff and the main body may be connected to each other through an elongated tube to supply fluid from the main body to the cuff.

The sphygmomanometer 1 of the embodiments above may be formed as a multi-functional, wrist-watch-type wearable device.

As is described above, a sphygmomanometer of the present disclosure is a sphygmomanometer including:

a first fluid bag that is to be worn around a measurement site, and turns into a pressurized state or an unpressurized state by supply or discharge of fluid;

a first and second pulse wave sensors that are mounted on the first fluid bag in a manner to be spaced from each other with respect to the width direction of the first fluid bag, and detect pulse waves of the respective opposing portions of an artery running along the measurement site;

a pressing part that locally presses the areas corresponding to the first and second pulse wave sensors with respect to the circumferential direction of the first fluid bag from the outer circumference side of the first fluid bag, which is the other side of the inner circumference side where the first and second pulse wave sensors are mounted;

a first blood pressure calculation part that calculates blood pressure based on pulse transit time obtained from the outputs of the first and second pulse wave sensors, with the first fluid bag being in an unpressurized state, and the first and second pulse wave sensors being pressed by the pressing force of the pressing part; and, a second blood pressure calculation part that calculates blood pressure based on the pressure within the first fluid bag with the first fluid bag being in a pressurized state for oscillometric blood pressure measurement.

As used herein, the "measurement site" refers to a site along which an artery runs. The measurement site may be, for example, an upper limb, such as a wrist or an upper arm, or a lower limb, such as an ankle or a thigh.

Also, the "fluid bag" refers to a bag-shaped member capable of containing a fluid, whatever it may be called. For example, it may be called a "cuff" instead of a fluid bag. The "fluid" can contain both a liquid and a gas, and for example, water or air may be used.

The "width direction" of the fluid bag corresponds to the longitudinal direction of the measurement site.

In the sphygmomanometer of the present disclosure, the first and second pulse wave sensors are mounted on the first fluid bag in a manner to be spaced from each other in the width direction of the first fluid bag. The pressing part that locally presses the areas corresponding to the first and second pulse wave sensors with respect to the circumferential direction of the first fluid bag is provided on the outer circumference side of the first fluid bag, which is the other side of the inner circumference side where the first and second pulse wave sensors are mounted. When pulse transit time-based blood pressure measurement is performed, fluid is discharged from the first fluid bag to turn the first fluid bag into an unpressurized state. The pressing part then presses the first and second pulse wave sensors against the measurement site with, for example, a certain pressing force. In this state, the first blood pressure calculation part calculates blood pressure based on pulse transit time obtained from outputs of the first and second pulse wave sensors. In this case, although the first fluid bag is present between the pressing part and the first and second pulse wave sensors, the first fluid bag is in an unpressurized state, and thus does not hinder the pressing part from pressing the first and second pulse wave sensors. This enables measurement of the first and second pulse wave signals under appropriate measurement conditions, and accordingly enables accurate pulse transit time-based blood pressure measurement. To perform oscillometric blood pressure measurement, fluid is supplied to the first fluid bag being worn around the measurement site to turn the first fluid bag into a pressurized state, which presses the first and second pulse wave sensors against the measurement site with, for example, a certain pressing force. In this state, the second blood pressure calculation part calculates blood pressure based on the pressure within the fluid. No other member (for example, a pressing plate) is present between the first fluid bag and the first and second pulse wave sensors, and thus the first fluid bag can sufficiently press the measurement site to sufficiently close the blood vessel. This enables accurate oscillometric blood pressure measurement. Thus, the present invention enables the simple-structured sphygmomanometer alone to perform accurate pulse transit time-based blood pressure measurement and oscillometric blood pressure measurement, and to perform calibration necessary for pulse transit time-based blood pressure measurement appropriately.

In the sphygmomanometer according to an embodiment, the pressing part includes a belt to be worn around the measurement site;

an expandable member arranged on the inner circumference side of the belt, which is closer to the measurement site than the belt, and expandable and contractible in the thickness direction of the belt; and a solid arranged at a position corresponding to the first and second pulse wave sensors on the inner circumference side of the expandable member, which is closer to the measurement site than the expandable member.

In this embodiment, the "belt" refers to a strip-shaped member to be worn around the measurement site, whatever it may be called. For example, it may be called a "band" or a "cuff" instead of a belt.

In the sphygmomanometer of this embodiment, pulse transit time-based blood pressure is measured with the belt being worn around the measurement site and the first fluid bag, from which fluid has been discharged, being in an unpressurized state. In this state, the pressing part expands the expandable member arranged on the inner circumference side of the belt to allow the first and second pulse wave sensors to be locally pressed by the belt, the expandable member, and the solid arranged at a position corresponding to the first and second pulse wave sensors on the inner circumference side of the expandable member. Thus, each of the first and second pulse wave sensors can be pressed with an appropriate pressing force. This enables accurate pulse transit time-based blood pressure measurement.

In a pulse wave measurement device according to an embodiment, the expandable member is a second fluid bag that turns into a pressurized state or an unpressurized state by supply or discharge of fluid.

In the sphygmomanometer of this embodiment, supplying fluid to the second fluid bag, which is the expandable member, turns the expandable member into a pressurized state to locally press the first and second pulse wave sensors via the solid. This enables accurate pulse transit time-based blood pressure measurement. On the other hand, discharging fluid from the second fluid bag, or the expandable member, turns the expandable member into an unpressurized state. With the belt worn around the measurement site, supplying fluid to the first fluid bag, on which the first and second pulse wave sensors are mounted, turns the first fluid bag into a pressurized state to sufficiently press the measurement site. This enables accurate oscillometric blood pressure measurement. Further, using the second fluid bag as the expandable member enables the second fluid bag and the first fluid bag worn around the measurement site to be used by changeover of a pump. This enables unified control.

In an embodiment of the sphygmomanometer, the first and second pulse wave sensors each include a pair of detection electrodes that detects the voltage of an opposing area.

In the sphygmomanometer of this embodiment, the pairs of detection electrodes of the first and second pulse wave sensors detect voltages of their respective opposing areas of the artery running along the measurement site, and pulse wave signals can be obtained using the impedance method. Thus, with a simple structure, pulse transit time-based blood pressure measurement is performed. Such pairs of detection electrodes can also be formed flat using, for example, plate-like or sheet-like soft electrodes. In that case, the pairs of detection electrodes do not hinder the first fluid bag from pressing the measurement site, and thus do not reduce accuracy of oscillometric blood pressure measurement.

The sphygmomanometer according to an embodiment includes
- a cross-correlation coefficient calculation part that calculates a cross-correlation coefficient between the waveforms of the first and second pulse wave signals obtained from outputs in time sequence of the first and second pulse wave sensors; and
- a pressing force setting part that sets the pressing force by the expandable member such that the cross-correlation coefficient calculated by the cross-correlation coefficient calculation part exceeds a predetermined threshold.

As used herein, the "cross-correlation coefficient" refers to a sample correlation coefficient (which is also referred to as Pearson product-moment correlation coefficient). For example, when two groups of numbers, a data sequence {xi} and a data sequence {yi} (where i=1, 2, . . . , n) are given, the cross-correlation coefficient r of the data sequence {xi} and the data sequence {yi} is defined by the equation (Eq. 1) shown in FIG. 12. x and y with an overbar in the equation (Eq. 1) denote their respective average numbers.

In the sphygmomanometer of this embodiment, with the fluid bag being worn around the measurement site, the pressing member presses the first and second pulse wave sensors, for example, with a certain pressing force against the measurement site. In this state, the first and second pulse wave sensors detect pulse waves of the respective opposing areas of the artery running along the measurement site. The cross-correlation coefficient calculation part obtains the first and second pulse wave signals output by the first and second pulse wave sensors, and calculate a cross-correlation coefficient between waveforms of the pulse wave signals. The pressing force setting part sets a pressing force by the expandable member among the pressing members such that the cross-correlation coefficient calculated by the cross-correlation coefficient calculation part exceeds a predetermined threshold. In this state, the first blood pressure calculation part calculates blood pressure based on pulse transit time obtained from the outputs of the first and second pulse wave sensors. This enhances accuracy in measurement of pulse transit time, and accordingly enhances accuracy of pulse transit time-based blood pressure measurement. This also enables acquisition of pulse transit time without increasing the pressing force for pressing the measurement site more than necessary. This can reduce the physical burden on the user.

In another aspect, the method for blood pressure measurement of the present invention includes:
preparing
- a first fluid bag that is to be worn around a measurement site, and turns into a pressurized state or an unpressurized state by supply or discharge of fluid,
- first and second pulse wave sensors that are mounted on the first fluid bag in a manner to be spaced from each other in a width direction of the first fluid bag, and detect pulse waves of respective opposing areas of an artery running along the measurement site, and
- a pressing part that locally presses areas corresponding to the first and second pulse wave sensors from an outer circumference side, which is the other side of the inner circumference side of the first fluid bag where the first and second pulse wave sensors are mounted;

turning the first fluid bag into an unpressurized state, pressing the first and second pulse wave sensors with a pressing force of the press part, and calculating, in this state, blood pressure based on pulse transit time obtained from outputs of the first and second pulse wave sensors for pulse transit time-based blood pressure measurement; and turning the first fluid bag into a pressurized state, and calculating blood pressure based on a pressure within the first fluid bag for oscillometric blood pressure measurement.

The method for blood pressure measurement according to the present invention enables accurate measurement of pulse transit time-based blood pressure and oscillometric blood pressure.

In yet another aspect, the device according to the present invention includes blood pressure measurement elements, wherein the blood pressure measurement elements include:
- a first fluid bag that is to be worn around a measurement site, and turns into a pressurized state or an unpressurized state by supply or discharge of fluid, first and second pulse wave sensors that are mounted on the first fluid bag in a manner to be spaced from each other in a width direction of the first fluid bag, and detect pulse waves of their respective opposing areas of an artery running along the measurement site,
- a pressing part that locally presses areas corresponding to the first and second pulse wave sensors with respect to the circumferential direction of the first bag from the outer circumference side, which is the other side of the inner circumference side of the first fluid bag where the first and second pulse wave sensors are mounted,
- a first blood pressure calculation part that calculates blood pressure based on pulse transit time obtained from outputs from the first and second pulse wave sensors with the first fluid bag being in an unpressurized state, and the first and second pulse wave sensors being pressed by a pressing force of the pressing part, and
- a second blood pressure calculation part that calculates blood pressure based on the pressure within the first fluid bag with the first fluid bag being in a pressurized state for oscillometric blood pressure measurement.

The "device" according to the present invention widely encompasses devices having a blood pressure measuring function, and may be formed, for example, as a multi-functional, wrist-watch-type wearable device, such as a smart watch.

The device according to the present invention enables a simple-structured sphygmomanometer alone to accurately measure both pulse transit time-based blood pressure and oscillometric blood pressure, and to appropriately perform calibration necessary for pulse transit time-based blood pressure measurement.

As clear from above, the sphygmomanometer, the blood measurement method, and the device according to the present invention enable accurate measurement of both pulse transit time-based blood pressure and oscillometric blood pressure.

The embodiments above are mere examples, and may be variously modified without departing from the scope of the invention. Although the embodiments described above may be independently implemented, the embodiments can be combined. Although the features of different embodiments can be independent from one another, the features of different embodiments can also be combined.

The invention claimed is:

1. A sphygmomanometer, comprising:
a first fluid bag that is configured to: (i) be worn on a wrist that is a measurement site so as to extend in a circumferential direction around the measurement site, and (ii) turn into a pressurized state or an unpressurized state by supply or discharge of fluid;
first and second pulse wave sensors that are mounted on an inner circumference of the first fluid bag at positions spaced from each other in a width direction of the first fluid bag, the width direction being transverse to the circumferential direction, the first and second pulse wave sensors being configured to:
be arranged at different positions along an artery in the measurement site in a worn state in which the first fluid bag is worn on the measurement site, and
detect pulse waves at the different positions at which the first and second pulse wave sensors are arranged;
a belt that is arranged on an outer circumferential side of the first fluid bag, and is configured to be worn around the measurement site;
an expandable member that is arranged on an inner circumference of the belt, closer to the measurement site than the belt, and is expandable and contractible in a thickness direction of the belt;
a plate-shaped member that is arranged on an inner circumference of the expandable member and on an outer circumference of the first fluid bag, closer to the measurement site than the expandable member at a position corresponding to the first and second pulse wave sensors; and
a central processing unit that is configured to:
calculate blood pressure based on a pulse transit time obtained from outputs from the first and second pulse wave sensors, with the first fluid bag in the unpressurized state, the expandable member in an expanded state, and the first and second pulse wave sensors being pressed by a pressing force of the belt, the expandable member, and the plate-shaped member, and
calculate blood pressure based on a pressure within the first fluid bag with the first fluid bag in the pressurized state and the expandable member in a contracted state for an oscillometric blood pressure measurement, without using the first and second pulse wave sensors,
wherein the first and second pulse wave sensors each include a pair of detection electrodes that are configured to detect a voltage at the different positions.

2. The sphygmomanometer according to claim 1, wherein the expandable member is a second fluid bag that is configured to turn into a pressurized state, which is the expanded state, or an unpressurized state, which is the contracted state, by supply or discharge of fluid.

3. The sphygmomanometer according to claim 1, wherein the central processing unit is further configured to:
obtain first and second pulse wave signals output in time sequence from the first and second pulse wave sensors, and calculate a cross-correlation coefficient between waveforms of the first and second pulse wave signals, and
set a pressing force exerted by the expandable member such that the cross-correlation coefficient calculated by the central processing unit exceeds a predetermined threshold.

4. A blood pressure measurement method, comprising:
preparing:
a first fluid bag that is configured to: (i) be worn on a wrist that is a measurement site so as to extend in a circumferential direction around the measurement site, and (ii) turn into a pressurized state or an unpressurized state by supply or discharge of fluid,
first and second pulse wave sensors that are mounted on an inner circumference of the first fluid bag at positions spaced from each other in a width direction of the first fluid bag, the width direction being transverse to the circumferential direction, the first and second pulse wave sensors being configured to:
be arranged at different positions along an artery in the measurement site in a worn state in which the first fluid bag is worn on the measurement site, and
detect pulse waves at the different positions at which the first and second pulse wave sensors are arranged,
a belt that is arranged on an outer circumferential side of the first fluid bag, and is configured to be worn around the measurement site,
an expandable member that is arranged on an inner circumference of the belt, closer to the measurement site than the belt, and is expandable and contractible in a thickness direction of the belt, and
a plate-shaped member that is arranged on an inner circumference of the expandable member and on an outer circumference of the first fluid bag, closer to the measurement site than the expandable member at a position corresponding to the first and second pulse wave sensors,
turning the first fluid bag into the unpressurized state, expanding the expandable member to an expanded state, pressing the first and second pulse wave sensors with a pressing force of the belt, the expandable member, and the plate-shaped member, and calculating blood pressure based on a pulse transit time obtained from outputs of the first and second pulse wave sensors for a pulse transit time-based blood pressure measurement; and
turning the first fluid bag into the pressurized state, contracting the expandable member to a contracted state, and calculating blood pressure based on a pressure within the first fluid bag for an oscillometric blood pressure measurement, without using the first and second pulse wave sensors,
wherein the first and second pulse wave sensors each include a pair of detection electrodes that are configured to detect a voltage at the different positions.

5. A device, comprising:
blood pressure measurement elements including:
a first fluid bag that is configured to: (i) be worn on a wrist that is a measurement site so as to extend in a circumferential direction around the measurement site, and (ii) turn into a pressurized state or an unpressurized state by supply or discharge of fluid, first and second pulse wave sensors that are mounted on an inner circumference of the first fluid bag at positions spaced from each other in a width direction of the first fluid bag, the width direction being transverse to the circumferential direction, the first and second pulse wave sensors being configured to:

be arranged at different positions along an artery in the measurement site in a worn state in which the first fluid bag is worn on the measurement site, and detect pulse waves at the different positions at which the first and second pulse wave sensors are arranged, an expandable member is expandable and contractible in a thickness direction, and a central processing unit that is configured to:

calculate blood pressure based on a pulse transit time obtained from outputs from the first and second pulse wave sensors with the first fluid bag being in the unpressurized state, the expandable member being in an expanded state, and the first and second pulse wave sensors being pressed by a pressing force against the measurement site, and calculate blood pressure based on a pressure within the first fluid bag with the first fluid bag being in the pressurized state and the expandable member being in a contracted state for an oscillometric blood pressure measurement, without using the first and second pulse wave sensors, wherein the first and second pulse wave sensors each include a pair of detection electrodes that are configured to detect a voltage at the different positions.

* * * * *